(12) United States Patent
Freeburg, II et al.

(10) Patent No.: US 11,004,546 B2
(45) Date of Patent: May 11, 2021

(54) AUTOMATED CONSTRUCTION OF PATIENT CARE GIVER TOOL USER INTERFACE USING THREE-TIERED ARCHITECTURE

(71) Applicant: CURANTIS SOLUTIONS, Addison, TX (US)

(72) Inventors: Robert Parker Freeburg, II, Addison, TX (US); Rishi Suresh Keshav, Addison, TX (US); Mohsin Nisar, Addison, TX (US)

(73) Assignee: CURANTIS SOLUTIONS, Addison, TX (US)

( * ) Notice: Subject to any disclaimer, the term of this patent is extended or adjusted under 35 U.S.C. 154(b) by 45 days.

(21) Appl. No.: 16/186,461

(22) Filed: Nov. 9, 2018

(65) Prior Publication Data
US 2020/0152297 A1    May 14, 2020

(51) Int. Cl.
| | |
|---|---|
| *G06F 17/00* | (2019.01) |
| *G16H 10/20* | (2018.01) |
| *G06F 40/174* | (2020.01) |
| *G06F 40/186* | (2020.01) |
| *G06F 40/197* | (2020.01) |
| *G06F 3/0481* | (2013.01) |

(52) U.S. Cl.
CPC ........... *G16H 10/20* (2018.01); *G06F 40/174* (2020.01); *G06F 40/186* (2020.01); *G06F 40/197* (2020.01); *G06F 3/0481* (2013.01)

(58) Field of Classification Search
CPC .... G06F 17/243; G06F 15/177; G06F 40/186; G16H 10/20

USPC ......................................... 715/222, 200, 221
See application file for complete search history.

(56) References Cited

U.S. PATENT DOCUMENTS 7,590,932 B2 * 9/2009 Britton .................. G06F 40/174
715/222
7,707,169 B2 * 4/2010 Comaniciu ............ G16H 10/60
707/602

(Continued)

OTHER PUBLICATIONS

Freeburg II, Robert Parker, et al., "Automated Triggering of Updates in Patient Plan of Care," filed Nov. 9, 2018, U.S. Appl. No. 16/186,465.

(Continued)

*Primary Examiner* — Manglesh M Patel (57) ABSTRACT

A system for constructing a patient assessment user interface. The system comprises at least one processor, a data store, wherein the data store stores an assessment template in a format comprising a plurality of human readable attribute-value pairs, wherein the assessment template identifies the format of an assessment, a memory, and an assessment component stored in the memory. When executed by the at least one processor, the assessment component receives a request for an assessment form from a patient care giver tool user interface (UI), creates an assessment form based on the assessment template, transmits the assessment form to the patient care giver tool UI, receives assessment input from the patient care giver tool UI, and stores the assessment input along with associated portions of the assessment template in the format comprising a plurality of human readable attribute-value pairs in a column of a table in the data store.

20 Claims, 7 Drawing Sheets

(56) References Cited

U.S. PATENT DOCUMENTS

| | | | |
|---|---|---|---|
| 7,742,931 B2* | 6/2010 | McElwain Miller | ........................ G06F 17/243 705/2 |
| 8,874,755 B1* | 10/2014 | Deklich | ................ G06F 9/5072 709/226 |
| 2002/0032385 A1 | 3/2002 | Raymond et al. | |
| 2002/0145634 A1* | 10/2002 | Gueramy | ............... G16H 10/60 715/840 |
| 2002/0170565 A1 | 11/2002 | Walker et al. | |
| 2010/0114609 A1 | 5/2010 | Duffy | |
| 2010/0138239 A1* | 6/2010 | Reicher | ................ G16H 10/20 705/3 |
| 2010/0241454 A1 | 9/2010 | Firminger | |
| 2011/0166885 A1 | 3/2011 | Walker | |
| 2011/0276349 A1* | 11/2011 | Huang | ................. G06Q 50/24 705/3 |
| 2012/0179482 A1 | 7/2012 | Garms et al. | |
| 2014/0122989 A1* | 5/2014 | Eigner | .................... H04L 67/30 715/226 |
| 2016/0210427 A1* | 7/2016 | Mynhier | ................ G16H 10/60 |
| 2016/0217256 A1* | 7/2016 | Kim | ........................ G16H 50/20 |
| 2018/0108125 A1* | 4/2018 | Beymer | ............. G06K 9/00442 |
| 2020/0152327 A1 | 5/2020 | Freeburg et al. | |

OTHER PUBLICATIONS

Freeburg II, Robert Parker, et al., "Automated Adaptation of Patient Assessment Report Format," filed Mar. 13, 2019, U.S. Appl. No. 16/352,720.

FAIPP Pre-Interview Communication dated Jan. 7, 2020, U.S. Appl. No. 16/352,720, filed Mar. 13, 2019.

Teodoro, Douglas et al. "ORBDA: An openEHR benchmark dataset for performance assessment of electronic health record servers." PLoS one vol. 13,1 e0190028. Jan. 2, 2018.

Liberati, Alessandro et al. "The PRISMA statement for reporting systematic reviews and meta-analyses of studies that evaluate health care interventions: explanation and elaboration." PLoS medicine vol. 6,7 (2009).

* cited by examiner

FIG. 6

AUTOMATED CONSTRUCTION OF PATIENT CARE GIVER TOOL USER INTERFACE USING THREE-TIERED ARCHITECTURE

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Patient care near the end of life may be partitioned into palliative care and hospice care. Hospice care is typically involved during the last six months of life or even just the last month of life. Hospice care is not typically directed to curing or restoring the health of the care patient but rather assuring their dignity and comfort as they approach death and possibly also assisting family and friends cope with the approaching death of the care patient. Palliative care may be involved over a longer period of time and precedes hospice care. Palliative care may be involved with helping patients maintain a good quality of life while in a slow decline caused by a chronic medical condition. Curative care, by contrast with both hospice care and palliative care, is directed to curing and/or restoring the care patient to a fully-functional health.

SUMMARY

In an embodiment, a method of dynamically constructing a patient assessment user interface using a three-tier architecture is disclosed. The method comprises storing an assessment template in a data store, wherein the assessment template is stored in a format comprising a plurality of human readable attribute-value pairs in a column of the data store and identifies the format of an assessment for each of a plurality of different assessment roles and assessment types and wherein the assessment template comprises a plurality of sections, receiving a request for an assessment form by an assessment component executing on a computer system from a patient care giver tool user interface (UI), and creating an assessment form by the assessment component based on an assessment type, based on a patient care giver role, and based on the assessment template. The method further comprises transmitting the assessment form by the assessment component to the patient care giver tool UI, receiving assessment input associated with a completed section of the assessment by the assessment component from the patient care giver tool UI, and storing the assessment input of the completed section of the assessment along with an associated section portion of the assessment template in the format comprising a plurality of human readable attribute-value pairs in a column of an entry associated with the completed section of the assessment in the data store. The method further comprises storing an updated version of the assessment template in the data store, wherein the updated version of the assessment template is stored in the format comprising a plurality of human readable attribute-value pairs in a column of the data store and identifies the format of an assessment for each of a plurality of different assessment roles and assessment types and wherein the updated version of the assessment template comprises a plurality of sections, receiving a second request for an assessment form by the assessment component from a patient care giver tool user interface (UI), and creating a second assessment form by the assessment component based on an assessment type, based on a patient care giver role, and based on the updated version of the assessment template. The method further comprises transmitting the second assessment form by the assessment component to the patient care giver tool UI, receiving assessment input associated with a completed section of the second assessment by the assessment component from the patient care giver tool UI, and storing the assessment input of the completed section of the second assessment along with an associated section portion of the updated version of the assessment template in the format comprising a plurality of human readable attribute-value pairs in a column of an entry associated with the completed section of the second assessment in the data store.

In another embodiment, a system for constructing a patient assessment user interface is disclosed. The system comprises at least one processor, a data store, wherein the data store stores an assessment template in a format comprising a plurality of human readable attribute-value pairs, wherein the assessment template identifies the format of an assessment for each of a plurality of different assessment roles and assessment types, a memory, and an assessment component stored in the memory. When executed by the at least one processor, the assessment component receives a request for an assessment form from a patient care giver tool user interface (UI), creates an assessment form based on an assessment type, based on a patient care giver role, and based on the assessment template, and transmits the assessment form to the patient care giver tool UI. The assessment component further receives assessment input from the patient care giver tool UI and stores the assessment input along with associated portions of the assessment template in the format comprising a plurality of human readable attribute-value pairs in a column of a table in the data store.

In yet another embodiment, an automated method of constructing a patient assessment user interface using a three-tiered architecture is disclosed. The method comprises storing an assessment template in a data store, wherein the assessment template is stored in a format comprising a plurality of human readable attribute-value pairs and identifies the format of an assessment for each of a plurality of different assessment roles and assessment types, receiving a request for an assessment form by an assessment component executing on a computer system from a patient care giver tool user interface (UI), creating an assessment form by the assessment component based on an assessment type, based on a patient care giver role, and based on the assessment template, and transmitting the assessment form by the assessment component to the patient care giver tool UI. The method further comprises receiving assessment input by the assessment component from the patient care giver tool UI, storing the assessment input along with associated portions of the assessment template in the format comprising a plurality of human readable attribute-value pairs in a column of a table in the data store, and updating a patient plan of care based on storing the assessment input, whereby care provided to a patient is adapted based on the received assessment input.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Typical health care is diagnostic driven and involves a kind of linear process of "solve for this" followed by "solve for that" actions. Hospice care is different and is not diagnostic driven but rather is plan of care driven. In hospice care, the patients are not expected to improve and recover and are experiencing a distinct decline in health that ends in their death. When federally allocated funds are involved in the hospice care, evidence of patient decline is desirably identified and documented by an interdisciplinary group (IDG). The IDG is populated by persons performing different roles, for example a doctor role, a nurse role, a spiritual advisor role, a social worker role, and a bereavement counselor role. The IDG meets periodically, for example about every two weeks, and findings of assessments of a patient at different IDG meetings are expected to manifest a trend of declining health of the patient. If, however, a patient exhibits signs of increasing health, they may be removed from hospice care.

Most patient care software tools are designed for typical health care, and often those patient care software tools are maladapted for use with the special needs involved in providing hospice care. Additionally, often care givers may use a plurality of different patient care tools that do not interoperate with each other and do not automatically share data on the same patient. Because of this lack of interoperability, care givers have to spend extra time jumping from one tool to a second tool and from the second tool back to the first tool to complete their work, which is inefficient. Additionally, this lack of interoperability interferes with members of an IDG accessing up to date information on hospice patients and interferes with meeting government regulations pertaining to qualification of patients for hospice reimbursement by the government. The present disclosure teaches a plan of care centric patient care giver tool system that is designed for providing hospice care. The patient care giver tool system taught herein is an integrated system that provides care givers seamless access to different tool functionalities from the same tool interface, and where the different tool functionalities have access to the same pool of patient data. The plan of care for each different patient is generated and maintained independently for each patient and reflects each patient's initial condition when admitted to hospice care and the history of the subsequent evolution of the patient's health. While much of the following is directed to examples involving hospice care, it is noted that the teachings herein may advantageously be adapted for use with palliative care, which also differs in similar ways from typical health care processes.

The present disclosure teaches a patient care giver tool system crafted for use in a hospice environment that dynamically constructs a patient assessment user interface for a patient care tool using a three-tiered architecture. The system is designed to efficiently and flexibly support hospice care activities. Hospice care may be funded by government funds and may be subject to tight government cost controls. Historically, the hospice care environment has been underserved by software tools specifically designed for the hospice care environment, possibly because it has been difficult to make a paying business out of hospice care, and without profits, hospice care organizations cannot fund development of the desired software tools. The patient care giver tool system taught herein proposes to solve this computing problem and this economic problem concurrently, through its efficiency and flexibility as described hereinafter.

To perform efficiently, the system is designed to support a plurality of independent hospice care organizations from a single multi-tenant execution platform, for example from a cloud computing environment. Additionally, the integrated nature of the system promotes efficiency of hospice care giver operations. The hospice care givers, using this system, need not move from a first tool to a second tool and back to the first tool to complete their work. They can complete their tasks using a single tool interface extended to their portable devices (e.g., a tablet computer) and work with an integrated data store containing all relevant data pertaining to their patients, and where the data is continuously up-to-date. For example, care giver inputs into an assessment of a hospice patient can immediately affect the plan of care of the hospice patient, and the same care giver may immediately see a new order or intervention in the patient's plan of care resulting from their input. In a different system that is not integrated, it is unlikely that an assessment input provided in an assessment tool would immediately percolate into a separate plan of care tool for example. Likewise, the assessment inputs can be accessed through the same system immediately by the members of the IDG in evaluating a patient's current status and to validate the patient's hospice care eligibility according to federal guidelines, because the system assessment microservice operates on the same data store as the IDG microservice operates on.

Flexibility is desirable, because different independent hospice care organizations are expected to demand different functionality in the patient care tool. Additionally, the needs of a hospice care organization are expected to change and drive differences in the functionality of the patient care tool as their processes evolve and government regulations change over time. To promote flexibility, the system is designed to define functional aspects that are expected to change using data definitions in JSON format rather than be defined in database schemas and hard coded in scripts or computer programs. Functional and structural aspects that are defined in JSON format can be revised much more quickly than database schemas, code, or scripts can be changed to implement similar revisions. The patient care tool is designed to flow this flexibility through a plurality of complementary functionalities, including an assessment microservice and an assessment reporting tool. For example, when changes are made to an assessment form by editing a JSON document defining the assessment format, this format change automatically flows with assessment input data to the assessment reporting tool, whereby the reports generated by the assessment reporting tool automatically adopt the new assessment format. JSON stands for JavaScript Object Notation.

The patient care giver tool system taught herein supports a role-based team care giving approach, where different personnel fulfilling the same role may be substituted for each other to provide patient care efficiently and timely. This team care giving approach promotes efficiency in scheduling delivery of care to patients, for example in choosing efficient driving routes to reduce driving mileage expenses. The team care giving approach promotes efficiency in completing IDG meetings to evaluate patients, where if one IDG member is called away in the middle of the IDG meeting—as sometimes happens in the hospice context—another person having the same role can substitute and the IDG meeting can continue without interruption. The patient care giver tool system supports a circulation process from assessments of patients to updates to a plan of care for each patient to the IDG meetings by providing shared access by each process step to the same body of patient data. In addition to promoting efficiency, this circulation process supports accuracy and prompt adaptation of the patient care plan.

The system provides different patient care functionalities from different microservices or modules that execute in a middle tier of the system architecture. For example, an assessment microservice is engaged for performing, recording, and reporting patient assessments. Other microservices may comprise one or more of a plan of care microservice, an interdisciplinary group (IDG) microservice, a scheduling microservice, an alerts and notifications microservice, a data analytics microservice, a history and event records microservice, a patient referral microservice, and a billing microservice. In an embodiment, at least some of the microservices extend a representational state transfer (REST) application programming interface (API) to a user interface (UI) application that executes in a front-end tier of the system architecture. In some contexts, the REST APIs may be referred to as RESTful APIs. A RESTful API uses hypertext transport protocol (HTTP) requests to GET, PUT, POST, and DELETE data. RESTful API technology provides some advantages such as relying on less bandwidth than a more robust communication technology such as simple object access protocol (SOAP).

In an embodiment, the UI application requests an assessment user interface format from the assessment microservice, processes the assessment user interface format to generate an assessment user interface document suitable to a specific user equipment (UE), and sends the assessment user interface document to the UE. The UE renders the assessment user interface document on a display of the UE and receives user inputs to controls presented in the display. The UE returns the user inputs to the UI application, and the UI application returns the user inputs to the assessment microservice via the RESTful API. The assessment microservice then acts upon the received user inputs, for example storing assessment data and assessment template data in a data store tier of the system architecture. In an embodiment, user interfaces of other microservices may likewise be automatically generated and sent to the UE in a manner similar to that described above for the assessment user interface.

Different types of assessments may be performed on patients. In an embodiment, the system supports an initial comprehensive assessment type, a comprehensive assessment type, a routine assessment type, an emergent assessment type, an in-patient assessment type, a continuous care assessment type, a watch assessment type, an even more care assessment type, a face-to-face assessment type, a phone call assessment type, and a supervisory visit assessment type. In different embodiments, the system may support fewer assessment types or more assessment types. Different assessment types may be associated with different assessment sections that are provided in the assessment user interface format (e.g., a first assessment type may be associated with an assessment user interface format comprising sections 1, 3, and 5 but not sections 2, 4, or 6 and a second assessment type may be associated with an assessment user interface format comprising sections 2, 4, and 6 but not sections 1, 3, or 5).

Additionally, different care givers may be associated with providing different care giver roles, and in an embodiment the assessment microservice provides different assessment user interface formats for different care giver roles. For example, different roles may be associated with different sections that may be incorporated in an assessment user interface format by the assessment microservice. Care giver roles may comprise one or more of a care manager role, a nurse role, a nurse practitioner role, a hospice aide role, a social worker role, a spiritual care role, a doctor role, a volunteer coordinator role, and a volunteer role. The nurse role may be provided by a registered nurse (RN). In some contexts, the doctor role may be referred to as a medical director role. A doctor role may be filled by a medical doctor or an orthopedic doctor. The definition of access to assessment sections based on care giver role may be defined in a matrix that is stored as data in the assessment data store in the data base tier of the system architecture.

An assessment user interface format comprises one or more section formats, each section format comprises one or more card formats, and each card format comprises one or more field formats. In an embodiment, the section formats, card formats, and field formats for a given hospice organization are defined in a JSON document that is stored in a JSON-B column of an assessment relational database in the data store tier of the system architecture. The JSON-B column promotes inclusion of unstructured data (the JSON document contents is deemed unstructured data in that there is no static structure defined for the data by a schema and the structure is rather indicated by the JSON document itself as human readable attribute-value pairs) within an otherwise structured data table entry. In some contexts the JSON document contained in the JSON-B column may be referred to as a JSON blob.

Different hospice organizations may provide different assessment type definitions and different format definitions, whereby to customize the assessment screens presented on UEs of hospice care givers of each different hospice organization. This definition may be referred to as an assessment template. The definition of the format of a section may be referred to as a section template; the definition of the format of a card may be referred to as a card template; and the format of a field may be referred to as a field template. By defining section formats, card formats, and field formats in JSON documents in JSON-B columns of tables in the data store tier, the system supports changing assessment interfaces based on changing the JSON document (e.g., changing data, configuring data) rather than based on changing database schemas, code, or scripts. Changing database schemas, computer code, and programming scripts may involve more effort—development effort, configuration control effort, software testing effort—than the effort involved in modifying data. The different assessment types and formats of different hospice organizations may be managed on the basis of differentiating between interface requests from UEs that identity themselves as associated with a specific hospice organization.

When a care giver completes a section of an assessment of a hospice patient and moves on to a different section, the completed section is stored by the assessment microservice in the data store in the data store tier. The assessment input data is stored and the format of the section template and field template likewise is stored in the data store in the data store tier. When the section data and format are stored, the assessment microservice accesses one or more scripts stored in the data store associated to the assessment section just stored. The assessment microservice executes each of the scripts, providing data from the assessment section to the script as input. In some cases, additional input may be provided to the script, for example assessment input from a different section of the assessment, a health condition of the patient, a level of care of the patient, or other input. If the script determines that the various input satisfies a criterion defined by the script (e.g., the script evaluates "true"), the script creates an issue and stores the issue in the plan of care associated with the patient undergoing assessment. When a hospice care giver having a qualified role next inspects the plan of care, she or he will take note of the issue created by the programming script in the plan of care data store and may adapt care provided to the hospice patient accordingly, for example by changing the plan of care on record for the patient which in turn flows into changed care being provided to the patient. In an example, the programming scripts are Groovy scripts.

Figure 1:
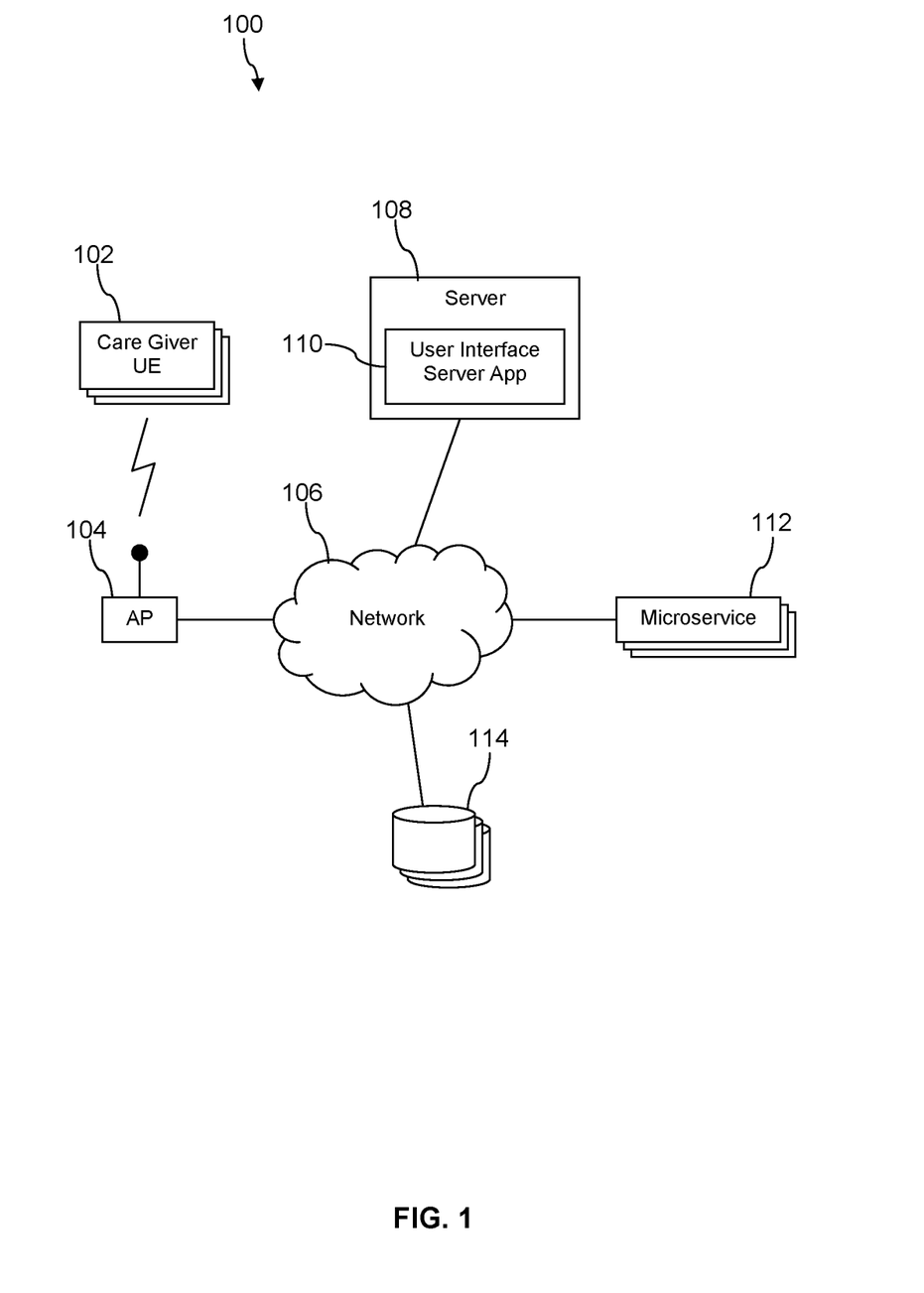
FIG. 1 is a block diagram of a system according to an embodiment of the disclosure.

Turning now to FIG. 1, a patient care giver tool system 100 is described. In an embodiment, the system 100 comprises a plurality of user equipments (UEs) 102, a wireless access point (AP) 104, a network 106, a server 108 executing a user interface server application 110, a plurality of microservices 112, and a plurality of data stores 114. The UEs 102 may be used by patient care givers to access a patient care tool user interface extended by the user interface server application 110. The patient care tool interface provides access to the microservices 112 and functionality that they support.

The UEs 102 may be tablet computers, notebook computers, laptop computers, mobile communication devices, or wearable computers. The network 106 comprises one or more public communication networks, one or more private communication networks, or a combination thereof. The wireless AP 104 may be a WiFi access point. The wireless AP 104 may be a cell site, such as a cell tower. In an embodiment, each of the microservices 112 may be provided by modules or applications that execute on server computers. In an embodiment, two or more of the microservices 112 may be hosted by the same server computer. In an embodiment, the user interface server application 110 may execute on the same server that hosts one or more of the microservices 112. In an embodiment, the data stores 114 may be provided by database management systems (DBMSs) executing on computer systems and providing mediated access to data storage. In an embodiment, the user interface server application 110, the microservices 112, and the data stores 114 may be provided by a cloud computing environment. In a cloud computing environment, the microservices 112 may execute in a multi-tenant mode of operation (e.g., serving a plurality of hospice care organizations at the same time).

The care giver UE 102 may present a user interface to the patient care giver tool system 100 that comprises a plurality of different views into the system 100. For example, the user interface on the care giver UE 102 may present an assessment section in a right hand side of the display, a plurality of assessment icons in a left hand side of the display, where the assessment icons promote selection of an assessment section, and a plan of care in a middle of the display. The plan of care may identify a patient name, a date of birth, an age, a primary diagnosis, and a secondary diagnosis. The plan of care may further provide a residential address of the patient, a level of care of the patient, a list of known allergies of the patient, a list of current medications of the patient, a case manager, an attending physician, and various care instructions. As the care giver completes sections of an assessment, he or she may save the assessment section. On selection of the save, the user interface server application 110 sends the data from the section to the assessment microservice 112, and the assessment microservice 112 stores both the input data and date defining the format of the section to a data store 114, for example in a JSON format in a JSON-B column of an entry in a Postgres database. In embodiment, assessment sections may comprise one or more of a vitals section, a neurological section, a pain section, a respiratory section, a cardiovascular section, a gastrointestinal section, a genitourinary section, a nutrition/metabolic section, a skin section, a musculoskeletal section, an ADLS/functional needs section, a precautions and safety section, a summary section, a face-to-face section, a supervisory visit section, and a hospice aide section.

Figure 2:
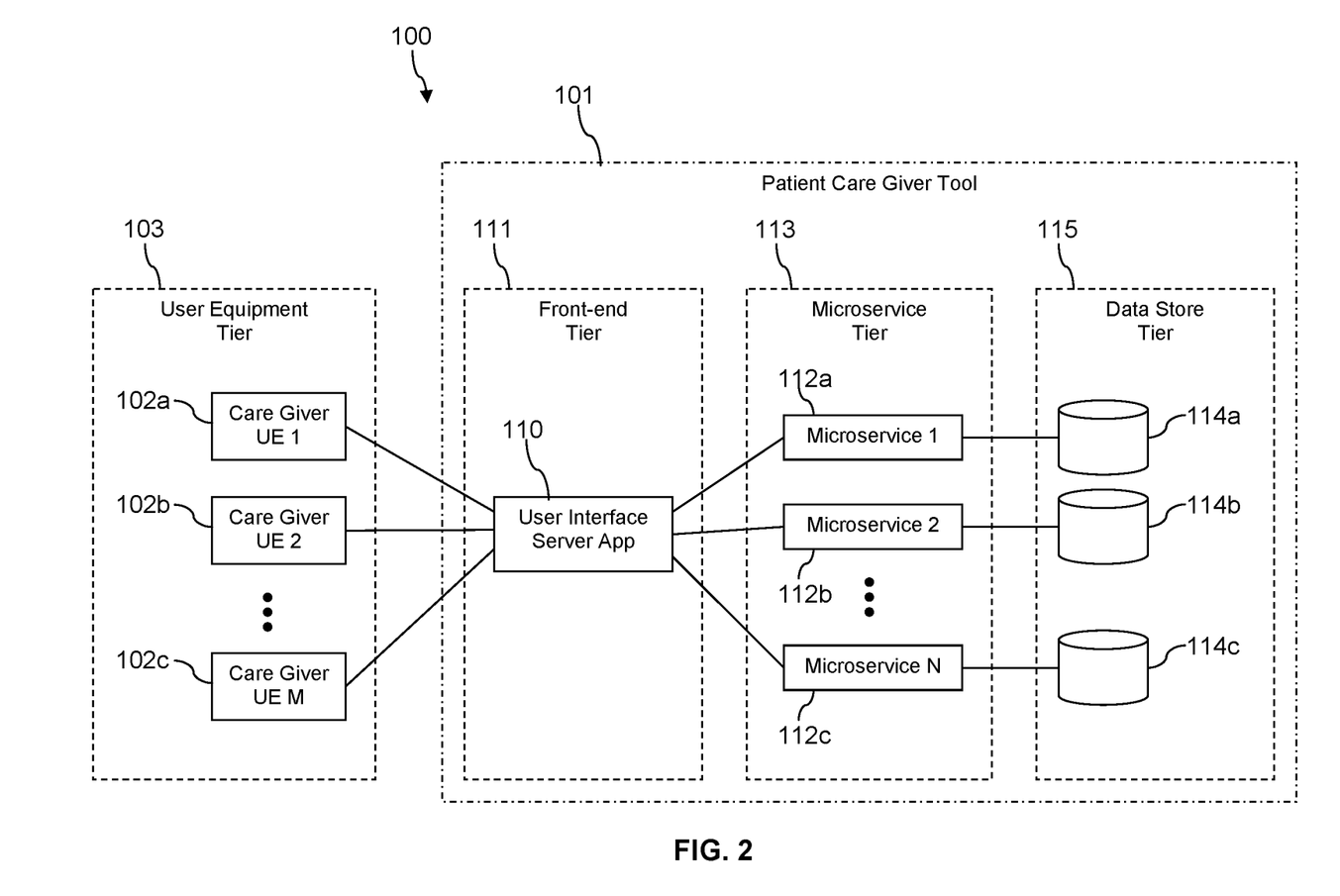
FIG. 2 is another block diagram of the system according to an embodiment, of the disclosure.

Turning now to FIG. 2, a different depiction of the patient care giver tool system 100 is described. While the depiction of system 100 in FIG. 1 illustrates communication linkages among elements of the system 100, the depiction of system 100 in FIG. 2 illustrates the three-tiered architecture and the functional relationships among the elements of the system 100. The patient care giver tool 101 comprises a front-end tier 111 comprising the user interface server application 110, a microservice tier 113 comprising a first microservice 112a, a second microservice 112b, and a third microservice 112c, and a data store tier 115 comprising a first data store 114a, a second data store 114b, and a third data store 114c. The system 100 further comprises what may be referred to as a user equipment tier 103 that comprises a first care giver UE 102a, a second care giver UE 102b, and a third care giver UE 102c. While three UEs 102 are illustrated in FIG. 2, it is understood that the UE tier 103 may comprise any number of UEs 102. While three microservices 112 are illustrated in FIG. 2, it is understood that the microservice tier 113 may comprise a greater number of microservices 112. For example, in an embodiment, the microservice tier 113 comprises an assessment microservice, a plan of care microservice, an interdisciplinary group (IDG) microservice, an alerts and notifications microservice, a patient referral microservice, and a billing microservice. While three data stores 114 are illustrated in FIG. 2, it is understood that the data store tier 115 may comprise any number of data stores. In an embodiment, the data store tier 115 comprises an assessment data store, a plan of care data store, an IDF data store, and an alerts and notifications data store. In an embodiment, the microservices 112 execute in a cloud computing environment in a multi-tenant mode of operation serving a plurality of patient care organizations, hospice care organizations, or palliative care organizations.

In an embodiment, the data stores 114 may be provided by a single data base management system (DBMS) and the data stores 114a, 114b, 114c may be independent sets of tables, where each independent set of tables is governed by its own database schema. In an embodiment, the data stores 114 are provided as a PostgreSQL DBMS. PostgreSQL is often referred to alternatively as Postgres. In an embodiment, the user interface server application 110 is developed as or based on an Angular application and an Ionic application. Angular is a TypeScript-based front-end development platform. Ionic is an HTML5 mobile application interface framework. Ionic is used to provide user interface look-and-feel presentation associated to the specific operating system of the UEs 102 (e.g., an Android look-and-feel for an Android UE operating system and an iOS look-and-feel for an Apple UE operating system).

When a hospice organization (or, alternatively, a palliative care organization) desires to configure an assessment section, card, or field, they may modify a template defining the format of the assessment in the data store 114 associated with the assessment microservice 112. This may entail editing a JSON document and storing it in a table of the data store 114, for example, in a JSON-B column of a Postgres database. Likewise, if the hospice organization desires to change the role based association of assessment sections, this can be accomplished by editing a JSON document and storing it in a table of the data store 114.

When the assessment template or the role based associations of the assessment template has been modified, the next time an assessment user interface is requested by the UE 102 from the user interface server application 110, the changed assessment format is used, without recoding, without recompiling, without generating a new schema. Each time a UE 102 selects a different assessment section for display on the UE 102, the subject assessment section is requested from the user interface server application 110. The user interface server application 110 requests the subject assessment section via the RESTful API extended by the assessment microservice 112. The assessment microservice 112 requests the appropriate assessment section template from the data store 114 associated with the assessment microservice 112.

The assessment microservice 112 parses the JSON document containing the desired template information and constructs an assessment section document based on the JSON document and based on the role associated with the UE 102. Because the template information retrieved from the data store 114 contains the changed assessment format and/or the changed role based associations of the assessment template, the assessment section document that the assessment microservice 112 constructs reflects the modification of the assessment template. As an example of role based access control, a nurse may be able to see a vitals assessment section, a neurological assessment section, a pain assessment section, and other assessment sections on his UE 102; but a hospice aid may be able to see a vitals assessment section but not be able to see a neurological assessment section or a pain assessment section on his UE 102. Note that the template does define these assessment sections, but the care giver role associated to the care giver (via the UE 102 request to the user interface server application 110 that contains the identity of the user which is itself mapped to a care giver role) is used to restrict what assessment sections may be seen on the UEs 102.

The assessment microservice 112 returns the constructed assessment section document via the RESTful API to the user interface server application 110. The user interface server application 110 adapts the constructed assessment section document for presentation on the UE 102 and sends the adapted assessment section document to the UE 102. The UE 102 then presents the subject assessment section in its display.

When the user inputs data into an assessment section and saves the section on the UE 102, the input data is returned to the user interface server application 110. The user interface server application 110 sends the input data via the RESTful API to the assessment microservice 112. The assessment microservice 112 saves the assessment section input data as well as the template format data associated with the assessment section in a new row in an assessment table, for example as JSON human readable attribute-value pairs in a JSON-B column of the assessment table. The assessment table may comprise other columns that are statically defined in a database schema, for example a patient identity column, a hospice organization identity column, a date and time column. The assessment microservice 112 populates appropriate values into these statically configured columns in the new entry in the assessment table.

When a section entry has been stored in the assessment table, in an embodiment the assessment microservice 112 launches a thread that requests the data for the assessment section just stored in the data store 114 and launches a separate thread that requests all scripts defined in the data store 114 for the subject assessment section. The assessment microservice 112 executes each script in turn. The scripts each evaluates one of the items of data stored in the assessment section against a criterion. If the value of the data item satisfies the criterion, the script creates an issue that it attaches to the plan of care associated with the patient. For example, a script may define a criterion that if the patient weight is 250 LBS or more, an issue should be attached to the patient plan of care.

In an embodiment, the scripts are programmed using the Groovy scripting language. Some of the microservices 112 are at least partially developed in the Java programming language, and Groovy is a scripting language that integrates smoothly with Java programs. In another embodiment, however, a different scripting language may be used to program the scripts, for example Perl or Ruby. The assessment microservice may be developed within a Spring Boot programming framework which automatically builds the RESTful API code extended for use by the assessment microservice 112 to the user interface server application 110. The Spring Boot programming framework simplifies developing a new application, relieving developers of creating repetitive structures, for example RESTful API code support.

When the user of the UE 102 completes an assessment and saves, the assessment microservice 112 accesses all the entries in the assessment table associated with that assessment (e.g., a row entry for each section of the assessment), creates a new JSON document containing input data and section template format data, and stores the new JSON document in a JSON-B column of a completed assessment table. In an embodiment, a report generation tool processes the new JSON document to create a report representing the completed assessment, for example a PDF file capturing the results of the completed assessment. In an embodiment, Jaspersoft is used to generate the report based on the JSON document.

Figure 3:
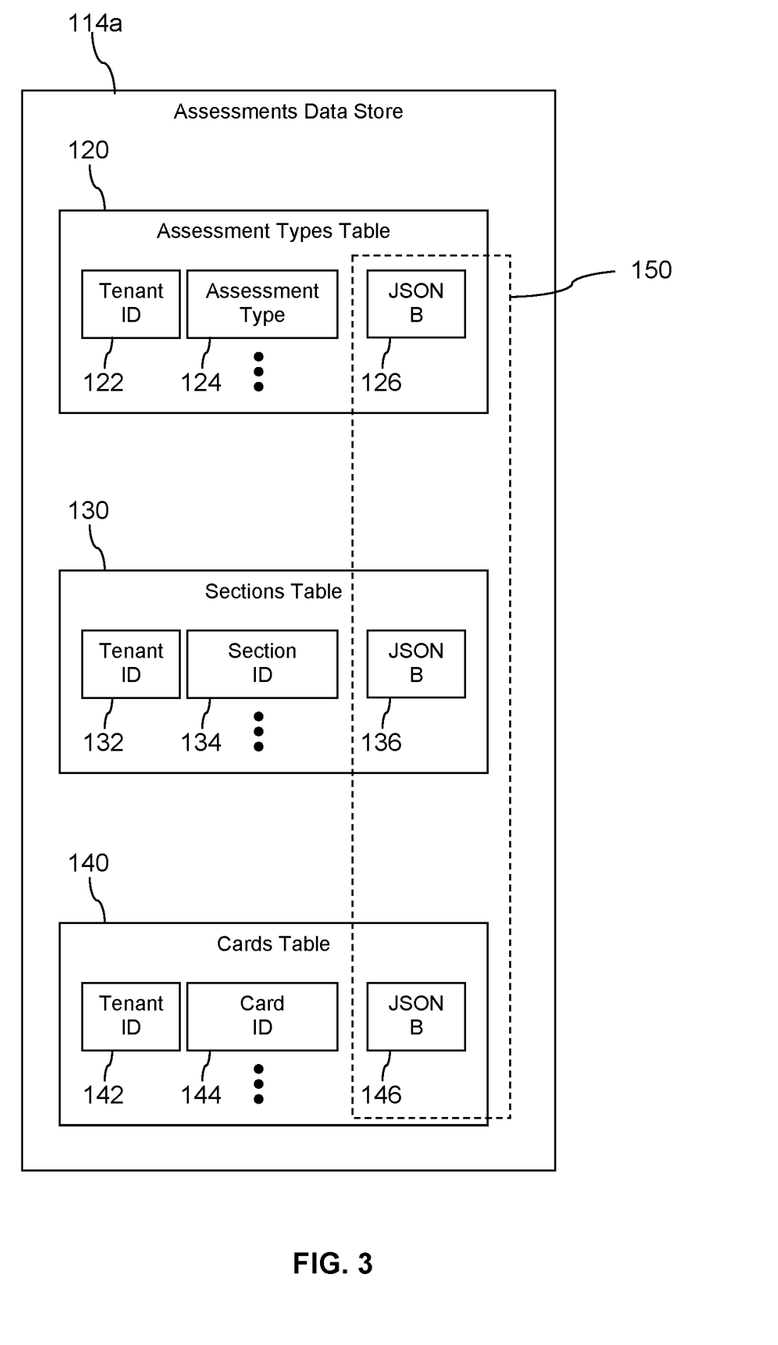
FIG. 3 is a block diagram of data store tables according to an embodiment of the disclosure.

Turning now to FIG. 3, exemplary data store tables are described. In an embodiment, the data store tier 115 comprises an assessments data store 114a that defines assessment templates used to provide an assessment form to be presented on the UE 102. The assessments data store 114a comprises an assessment types table 120, a sections table 130, and a cards table 140. Each row in the assessment types table 120 defines a format of an assessment type 124, for example in an assessment format JSON B column 126.

Example assessment types comprise an initial comprehensive assessment type, a comprehensive assessment type, a routine visit assessment type, and other assessment types. In some circumstances the assessment types table 120 may comprise a plurality of rows associated with the same assessment type 124, for example a plurality of rows defining different formats of initial assessment types 124. The different rows associated with the same assessment type 124 are distinguished by having different tenant IDs 122. A default definition of a format of an assessment type 124 may be created as a row in the assessment types table 120, for example a row having a tenant ID 122 of a null value, a zero value, or some other distinctive value that distinguishes it from a specific hospice organization. If a hospice organization wishes to define a custom assessment format for an assessment type 124 that deviates from the default format for the assessment type 124, a row may be added to the assessment types table 120 that identifies the assessment type 124, the tenant ID 122 (e.g., a unique identifier associated to the hospice organization), and defines the custom assessment format in the assessment format JSON B column 126. The assessment format JSON B column 126 may define the format of the assessment type as a plurality of sections that compose the assessment form.

Each row in the sections table 130 comprises a section identity 134 and defines a format of a section, for example in a section format JSON B column 136. The section format JSON B column 136 may define the format of the section as a plurality of cards that compose the section. In some circumstances, the sections table 130 may comprise a plurality of rows associated with the same section identity 134. The different rows in the sections table 130 associated with the same section identity are distinguished by having different tenant IDs 132. A default definition of a format for a section identity 134 may be created as a row in the sections table 130 having a tenant ID 132 that is distinctive value such as a null value or a zero value. If a hospice organization wishes to define a custom section format for a section identity 134 that deviates from the default format for the section identity 134, a row may be added to the sections table 130 that identifies the section identity 134, the tenant ID 132, and defining the custom section format in the section format JSON B column 136.

Each row in the cards table 140 defines a card identity 144 and defines a format of a card, for example in a card format JSON B column 146. The card format JSON B column 146 may define the format of the card as a plurality of fields that compose the card and further defines the layout of the fields. In some circumstances, the cards table 140 may comprise a plurality of rows associated with the same card identity 144. The different rows associated with the same card identity 144 are distinguished by having different tenant IDs 142. A default definition of a format for a card identity 144 may be created as a row in the cards table 140 having a tenant ID 142 having a null value, a zero value, or another distinctive value. If a hospice organization wishes to define a custom card format that deviates from the default card format defined for the card identity 144, a row may be added to the cards table 140 that identifies the card identity 144, the tenant ID 142, and defining the custom card format in the card format JSON B column 146.

The assessment type format JSON B column 126, the section format JSON B column 136, and card format JSON B column 146 associated with a given hospice organization may be viewed as an assessment format template 150 associated to that given hospice organization. It is understood that the assessment format template 150 may comprise some default format template components as well as some custom format template components. In some contexts, the section format JSON B 136 associated with a specific section ID 134 and a specific tenant ID 132 may be viewed as an assessment section format template or a section template. In some contexts, the card format JSON B 146 associated with a specific card ID 144 and a specific tenant ID 142 may be viewed as an assessment card format template or a card template. In another embodiment, the assessment format template 150 may be stored in a different way. In an embodiment, the assessments data store 114a comprises additional tables and data that are not illustrated in FIG. 3, for example tables storing information on completed sections (e.g., input data and section template information, as described further above), tables storing completed assessments, and other data.

Figure 4A:
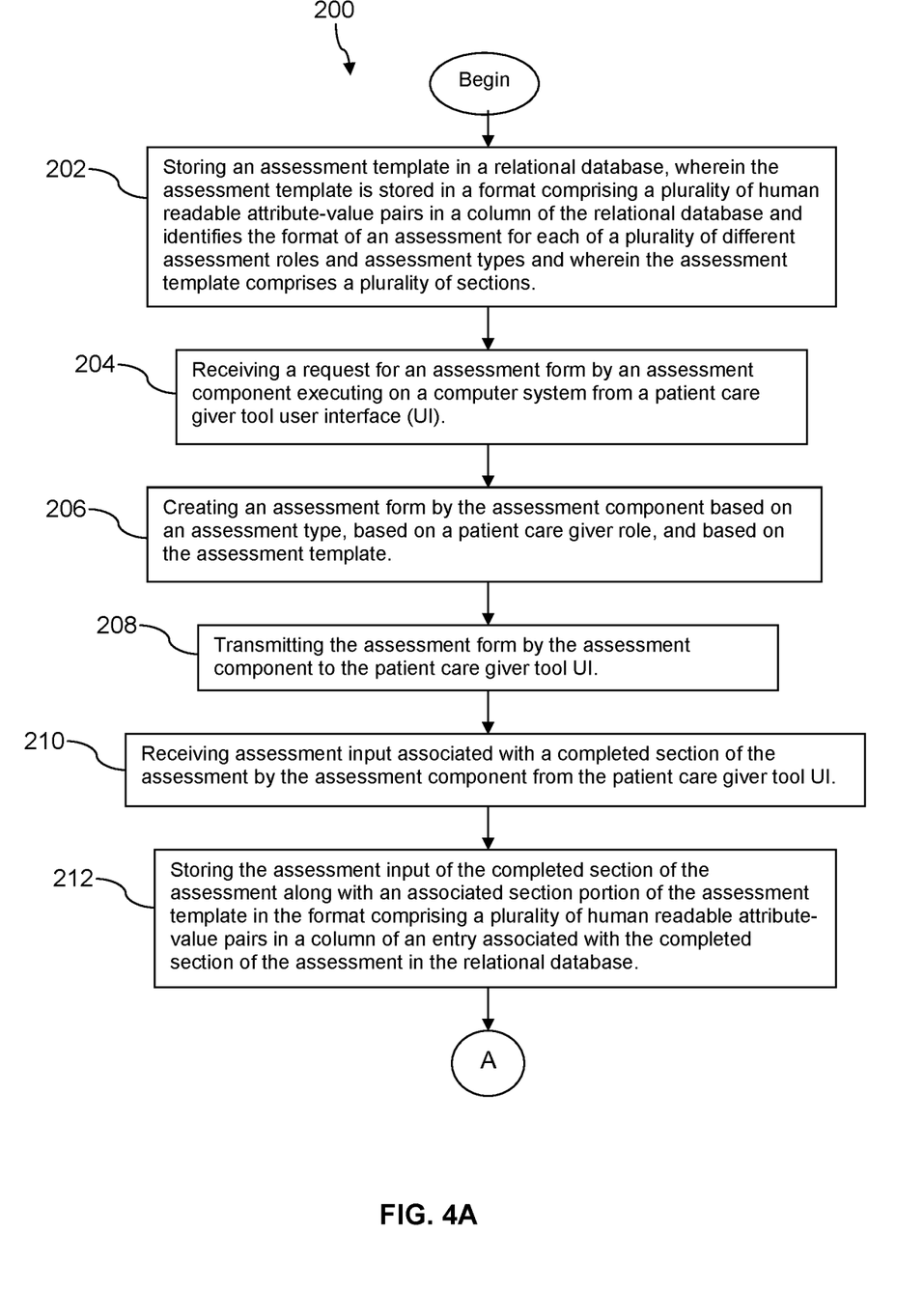
FIG. 4A and FIG. 4B are a flow chart of a method according to an embodiment of the disclosure.
Figure 4B:
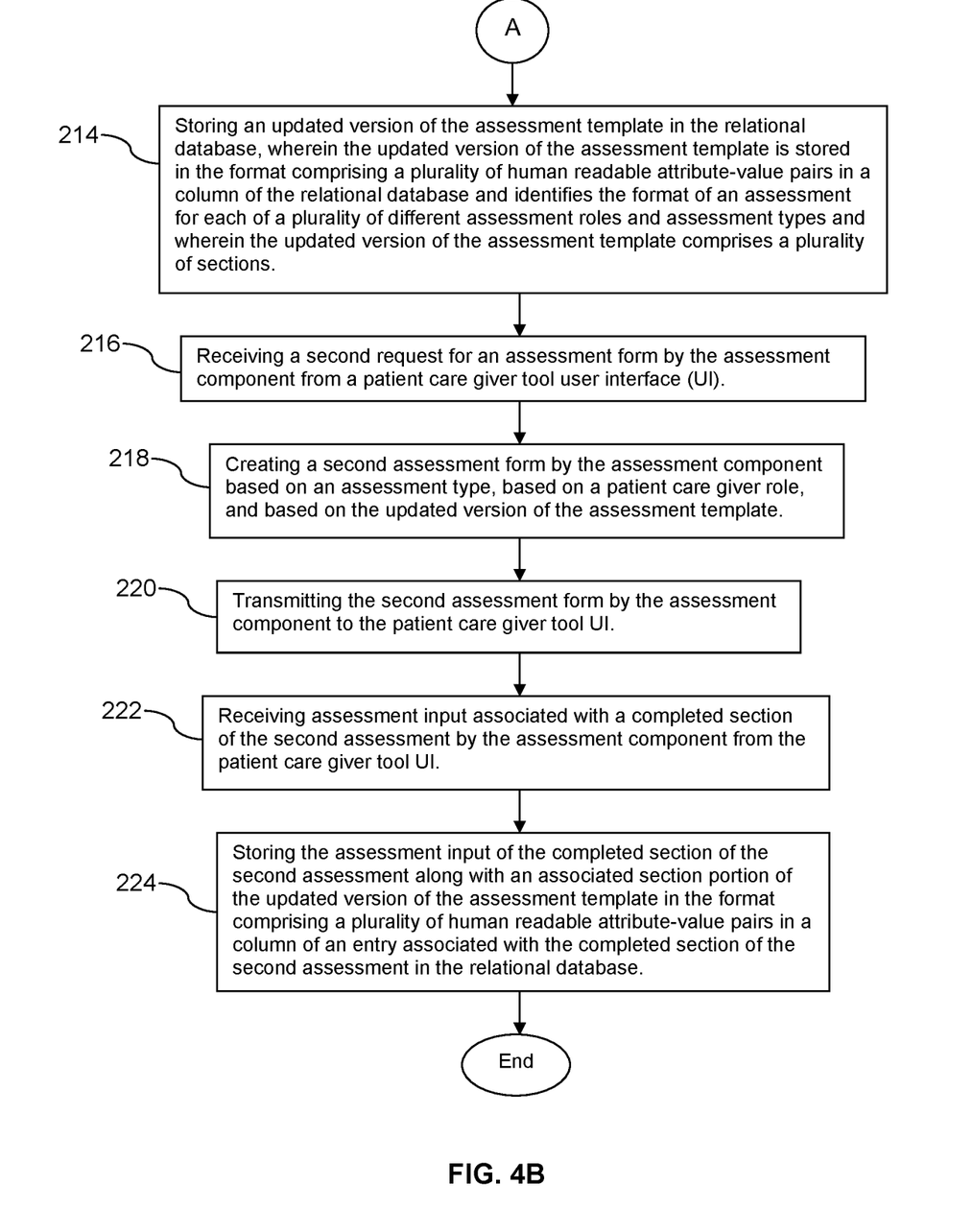

Turning now to FIG. 4A and FIG. 4B, a method 200 is described. In an embodiment, the method 200 is a method of dynamically constructing a patient assessment user interface using a three-tier architecture. The three-tier architecture is best seen in FIG. 2, where the three tiers are (A) a front-end tier 111, (B) a microservice tier 113, and (C) a data store tier 115. It is noted that this three-tier architecture supports the efficiency and flexibility goals established for the patient care giver tool 101.

At block 202, the method 200 comprises storing an assessment template in a relational database, wherein the assessment template is stored in a format comprising a plurality of human readable attribute-value pairs in a column of the relational database and identifies the format of an assessment for each of a plurality of different assessment roles and assessment types and wherein the assessment template comprises a plurality of sections. In an embodiment, the format comprising a plurality of human readable attribute-value pairs is a JSON format. In an embodiment, the relational database is the data store 114 in the data store tier 115. In an embodiment, the relational database is a PostgreSQL database (in some contexts PostgreSQL is referred to as a Postgres database). The assessment template stored during block 202 may be an initial assessment template established on first deploying the patient care giver tool 101. Alternatively, the assessment template stored during block 202 may be a revised assessment template, created by text editing the human readable attribute-value pairs, adding one or more human readable attribute-value pairs, and/or deleting one or more human readable attribute-value pairs.

The human readable attribute-value pairs may define sections, cards, and/or fields of the assessment form, for example defining section layouts in terms of cards, card layouts in terms of fields, field layout in terms of data types and data size or length. The human readable attribute-value pairs may define text to be displayed in sections, cards, and/or fields, for example names of sections, cards, and/or fields.

At block 204, the method 200 comprises receiving a request for an assessment form by an assessment component executing on a computer system from a patient care giver tool user interface (UI). In an embodiment, the patient care giver tool UI is the user interface server application 110. The assessment component may receive the request for the assessment form via a REST application programming interface (API) that it extends to the patient care giver tool UI. The request may identify a patient care giver role of the user of the UE 102 initiating an assessment. The request may identify an assessment type. The patient care giver role of the user of the UE 102 may be determined based on a login of the user. For example, every user granted a login to the patient care giver tool 101 may be predefined to be associated to a specific patient care giver role, e.g., one of a nurse role, a doctor role, a spiritual advisor role, or a social worker role.

At block 206, the method 200 comprises creating an assessment form by the assessment component based on an assessment type, based on a patient care giver role, and based on the assessment template. The assessment component may execute role based access control rules to select sections from a generic assessment template for creating the assessment form. Likewise, the assessment component may select some but not all of the sections from the generic assessment template based on the assessment type. In an embodiment, the processing of block 206 may further be based on an identity of a hospice organization and/or on a tenant ID. In an embodiment, the processing of block 206 may further be based on a level of care associated with the patient. In an embodiment, levels of care comprise routine home care, continuous care, respite care, and general in-patient care. In another embodiment, either fewer or more levels of care may apply.

At block 208, the method 200 comprises transmitting the assessment form by the assessment component to the patient care giver tool UI. In an embodiment, the assessment component transmits the assessment form via the REST API to the patient care giver UI. At block 210, the method 200 comprises receiving assessment input associated with a completed section of the assessment by the assessment component from the patient care giver tool UI. In an embodiment, the patient care giver tool UI sends the assessment input via the REST API. The assessment input may have been input by a user of the UE 102 and a save button in an assessment section screen may have been selected or the user may have navigated from a first assessment section display to a second assessment display on the UE 102.

At block 212, the method 200 comprises storing the assessment input of the completed section of the assessment along with an associated section portion of the assessment template in the format comprising a plurality of human readable attribute-value pairs in a column of an entry associated with the completed section of the assessment in the relational database. In an embodiment, the assessment input and the associated section portion of the assessment template are stored in JSON format in a JSON-B column of the relational database. In an embodiment, the assessment input and the associated section portion of the assessment template are stored in a new row entry in the relational database, where some information in the new row entry is formatted in statically structured columns of the new row entry and the assessment information and associated section portion of the assessment template are stored in an unstructured column of the new row entry. The statically structured columns of the new row entry may identify a patient, a hospice care organization, and a time and date.

At block 214, the method 200 comprises storing an updated version of the assessment template in the relational database, wherein the updated version of the assessment template is stored in the format comprising a plurality of human readable attribute-value pairs in a column of the relational database and identifies the format of an assessment for each of a plurality of different assessment roles and assessment types and wherein the updated version of the assessment template comprises a plurality of sections. The updated version of the assessment template stored during block 214 may be a revised assessment template, created by text editing the human readable attribute-value pairs, adding one or more human readable attribute-value pairs, and/or deleting one or more human readable attribute-value pairs. The assessment template may be updated by a hospice care organization or may be updated by a third party based on requirements defined by the hospice care organization. The assessment template may be updated to comply with additional regulatory requirements. The assessment template may be updated to improve a hospice care process of a hospice care organization.

At block 216, the method 200 comprises receiving a second request for an assessment form by the assessment component from a patient care giver tool user interface (UI). At block 218, the method 200 comprises creating a second assessment form by the assessment component based on an assessment type, based on a patient care giver role, and based on the updated version of the assessment template. In an embodiment, the processing of block 218 may further be based on an identity of a hospice organization and/or on a tenant ID. In an embodiment, the processing of block 218 may further be based on a level of care associated with the patient.

At block 220, the method 200 comprises transmitting the second assessment form by the assessment component to the patient care giver tool UI. It is understood that the second assessment form created based on the updated version of the assessment template is different in some way from the assessment form created in block 206. For example, the second assessment form may comprise one or more fields in an assessment section which were not present in the assessment form created at block 206. For example, the second assessment form may comprise a field that has a different input length than the same field in the assessment form created at block 206.

At block 222, the method 200 comprises receiving assessment input associated with a completed section of the second assessment by the assessment component from the patient care giver tool UI. At block 224, the method 200 comprises storing the assessment input of the completed section of the second assessment along with an associated section portion of the updated version of the assessment template in the format comprising a plurality of human readable attribute-value pairs in a column of an entry associated with the completed section of the second assessment in the relational database.

Figure 5:
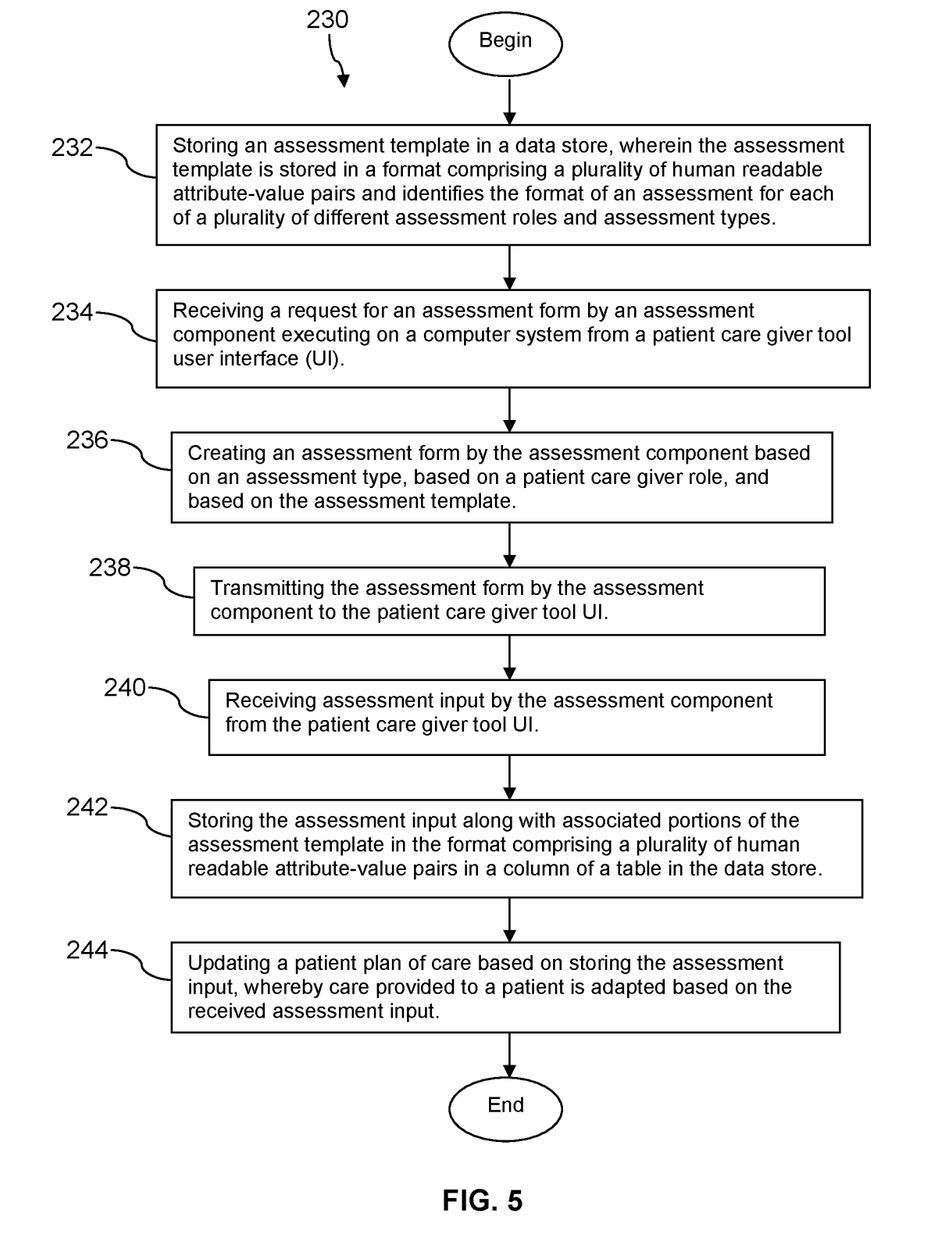
FIG. 5 is a flow chart of another method according to an embodiment of the disclosure.

Turning now to FIG. 5, a method 230 is described. In an embodiment, the method 230 is an automated method of constructing a patient assessment user interface using a three-tiered architecture. At block 232, the method 230 comprises storing an assessment template in a data store, wherein the assessment template is stored in a format comprising a plurality of human readable attribute-value pairs and identifies the format of an assessment for each of a plurality of different assessment roles and assessment types.

At block 234, the method 230 comprises receiving a request for an assessment form by an assessment component executing on a computer system from a patient care giver tool user interface (UI). At block 236, the method 230 comprises creating an assessment form by the assessment component based on an assessment type, based on a patient care giver role, and based on the assessment template. In an embodiment, the processing of block 236 may further be based on an identity of a hospice organization and/or on a tenant ID. In an embodiment, the processing of block 236 is further based on a level of care associated with the patient. At block 238, the method 230 comprises transmitting the assessment form by the assessment component to the patient care giver tool UI.

At block 240, the method 230 comprises receiving assessment input by the assessment component from the patient care giver tool UI. At block 242, the method 230 comprises storing the assessment input along with associated portions of the assessment template in the format comprising a plurality of human readable attribute-value pairs in a column of a table in the data store. At block 244, the method 230 comprises updating a patient plan of care based on storing the assessment input, whereby care provided to a patient is adapted based on the received assessment input. For example, at block 244, an issue is attached to the plan of care. The plan of care is reviewed in an interdisciplinary group (IDG) and a goal is added to the plan of care based on the issue. Based on the newly added goal, an intervention is added to the plan of care. When a hospice care giver next conducts a visit and/or assessment of the subject patient, the care giver provides care based on the newly added intervention. For example, the care giver encourages the patient to listen to classical music to relieve their boredom and depression. For example, the care giver encourages the patient to drink more water. For example, the care giver boosts a pain medication dosage. For example, the care giver spends time to ask the patient to tell a story from his or her youth.

Figure 6:
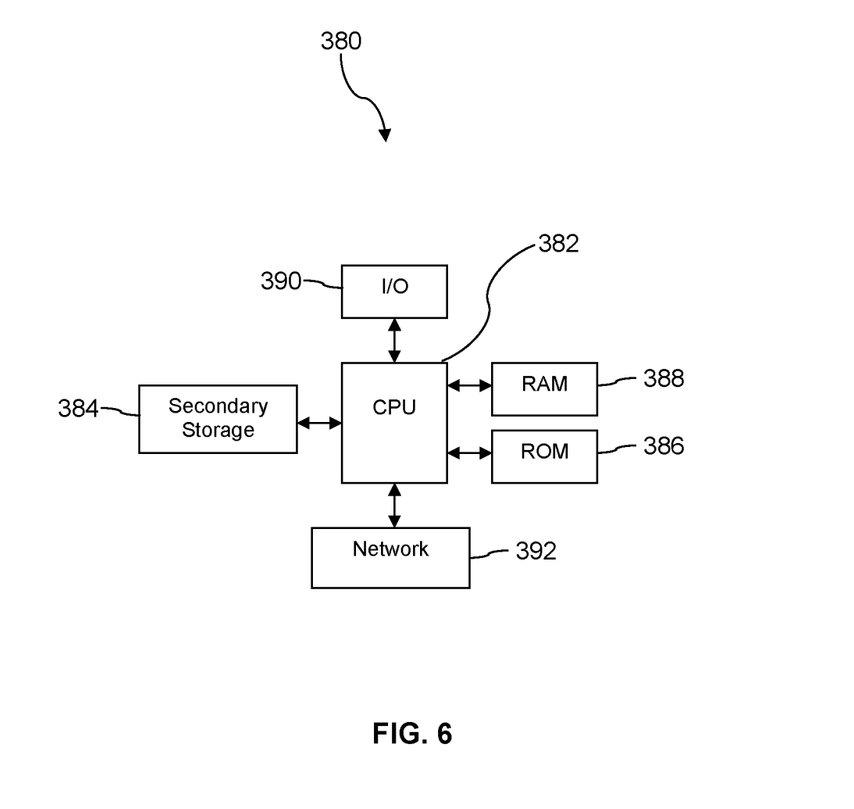
FIG. 6 is a block diagram of a computer system according to an embodiment of the disclosure.

FIG. 6 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the computer system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from a hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of dynamically constructing a patient assessment user interface using a three-tier architecture, comprising:

storing an assessment template in a data store, wherein the assessment template is stored in a format comprising a plurality of human readable attribute-value pairs in a column of the data store and identifies the format of an assessment for each of a plurality of different patient care giver assessment roles and assessment types, and wherein the assessment template comprises a plurality of sections including a first section and a second section;

receiving a request for an assessment form by an assessment component executing on a computer system from a patient care giver tool user interface (UI);

creating an assessment form for a patient care giver by the assessment component based on an assessment type to be performed on a patient by the patient care giver, based on a patient care giver role of the patient care giver, and based on the assessment template;

transmitting the assessment form by the assessment component to the patient care giver tool UI for presentation to the patient care giver;

receiving, by the assessment component from the patient care giver tool UI, assessment input associated with the first section of the assessment completed by the patient care giver, the assessment input inputted by the patient care giver;

storing the assessment input of the completed first section of the assessment along with the first section of the assessment template in the format comprising a plurality of human readable attribute-value pairs in a column of an entry associated with the completed first section of the assessment in the data store;

subsequently receiving, by the assessment component from the patient care giver tool UI, assessment input associated with the second section of the assessment completed by the patient care giver;

storing the assessment input of the completed second section of the assessment along with the second section of the assessment template in the format comprising a plurality of human readable attribute-value pairs in a column of an entry associated with the completed second section of the assessment in the data store;

storing an updated version of the assessment template in the data store, wherein the updated version of the assessment template is stored in the format comprising a plurality of human readable attribute-value pairs in a column of the data store and identifies the format of an assessment for each of a plurality of different assessment roles and assessment types and wherein the updated version of the assessment template comprises a plurality of sections;

receiving a second request for an assessment form by the assessment component from a second patient care giver tool user interface (UI);

creating a second assessment form by the assessment component based on an assessment type, based on a patient care giver role, and based on the updated version of the assessment template;

transmitting the second assessment form by the assessment component to the second patient care giver tool UI;

receiving assessment input associated with a completed section of the second assessment by the assessment component from the second patient care giver tool UI; and storing the assessment input of the completed section of the second assessment along with an associated section portion of the updated version of the assessment template in the format comprising a plurality of human readable attribute-value pairs in a column of an entry associated with the completed section of the second assessment in the data store.

2. The method of claim 1, wherein the format comprising a plurality of human readable attribute-value pairs is a JSON format.

3. The method of claim 1, wherein the data store is a PostgreSQL database.

4. The method of claim 1, wherein the patient assessment user interface is provided by a hospice care system.

5. The method of claim 1, wherein the patient assessment user interface is provided by a palliative care system.

6. The method of claim 1, wherein patient care giver roles comprise nurse, doctor, spiritual advisor, and social worker.

7. The method of claim 1, wherein the assessment type is one of a comprehensive assessment type, a routine assessment type, an emergent assessment type, an in-patient assessment type, a continuous care assessment type, a watch assessment type, an even more care assessment type, a face-to-face assessment type, a phone call assessment type, and a supervisory visit assessment type.

8. The method of claim 1, wherein the sections of the assessment template comprise at least five of a vitals section, a neurological section, a pain section, a respiratory section, a cardiovascular section, a gastrointestinal section, a genitourinary section, a nutrition/metabolic section, a skin section, a musculoskeletal section, an ADLS/functional needs section, a precautions and safety section, a summary section, a face-to-face section, a supervisory visit section, and a hospice aide section.

9. The method of claim 1, wherein the assessment component is based on a Spring Boot development framework.

10. The method of claim 9, wherein the assessment component extends a representational state transfer (REST) application programming interface (API) to the patient care giver tool UI for use by the patient care giver tool in requesting an assessment form and in receiving the assessment form.

11. A system for constructing a patient assessment user interface, comprising:

at least one processor;

a data store comprising an assessment template that includes a plurality of sections, wherein the assessment template defines the plurality of sections in a JSON document that is stored in the data store in a JSON format comprising a plurality of human readable attribute-value pairs in a JSON-B column, wherein the assessment template identifies the format of an assessment for each of a plurality of different patient care giver assessment roles and assessment types;

a memory; and an assessment component stored in the memory that, when executed by the at least one processor:
- receives a request for an assessment form from a patient care giver tool user interface (UI);
- creates an assessment form for a patient care giver based on an assessment type to be performed on a patient by the patient care giver, based on a patient care giver role of the patient care giver, and based on the assessment template;
- transmits the assessment form to the patient care giver tool UI for presentation to the patient care giver;
- receives assessment input associated with a completed section of the assessment from the patient care giver tool UI, the assessment input inputted by the patient care giver;
- stores the assessment input of the completed section of the assessment along with an associated section portion of the assessment template in the format comprising a plurality of human readable attribute-value pairs in a column of a table in the data store;
- modifies at least one section of the plurality of sections of the assessment template by changing the JSON document to create an updated version of the assessment template and stores the updated version of the assessment template in the data store, wherein the updated version of the assessment template is stored in the JSON format comprising a plurality of human readable attribute-value pairs in a JSON-B column of the data store and identifies the format of an assessment for each of a plurality of different assessment roles and assessment types and wherein the updated version of the assessment template comprises a plurality of sections;
- receives a request for the at least one section from the patient care giver tool UI;
- creates an assessment section document for the at least one section based on the updated version of the assessment template;
- transmits the assessment section document to the patient care giver tool UI;
- receives assessment input associated with the completed at least one section of the assessment from the patient care giver tool UI; and
- stores the assessment input of the completed at least one section of the assessment along with the at least one section of the updated version of the assessment template in the JSON format comprising a plurality of human readable attribute-value pairs in a JSON-B column of an entry associated with the completed at least one section of the assessment in the data store.

12. The system of claim 11, wherein the system is a cloud computing system.

13. The system of claim 12, wherein the assessment component is executed by the at least one processor in a multi-tenant mode of operation, serving a plurality of different hospice care organizations.

14. The system of claim 11, wherein the data store is a PostgreSQL data store.

15. An automated method of constructing a patient assessment user interface using a three-tiered architecture, comprising:
- storing an assessment template in a data store, wherein the assessment template is stored in a format comprising a plurality of human readable attribute-value pairs and identifies the format of an assessment for each of a plurality of different assessment patient care giver roles and assessment types, and wherein the assessment template comprises a plurality of sections;
- receiving a request for an assessment form by an assessment component executing on a computer system from a patient care giver tool user interface (UI);
- creating an assessment form for a patient care giver by the assessment component based on an assessment type to be performed on a patient by the patient care giver, based on a patient care giver role of the patient care giver, and based on the assessment template;
- transmitting the assessment form by the assessment component to the patient care giver tool UI for presentation to the patient care giver;
- receiving assessment input associated with a completed section of the assessment by the assessment component from the patient care giver tool UI, the assessment input inputted by the patient care giver;
- storing the assessment input of the completed section of the assessment along with an associated section portion of the assessment template in the format comprising a plurality of human readable attribute-value pairs in a column of a table in the data store;
- launching a script that retrieves the saved assessment section input data and one or more associated section trigger rules from the data store, wherein the one or more associated section trigger rules comprises one or more predefined criteria;
- evaluating the saved assessment section input data against the one or more predefined criteria;
- determining that the saved assessment section input data satisfies at least one of the one or more predefined criteria; and
- in response to the determination, updating a patient plan of care based on storing the assessment input, whereby care provided to a patient is adapted based on the received assessment input.

16. The method of claim 15, wherein the format comprising the plurality of human readable attribute-value pairs is a JSON format and where the column of the table in the data store in the JSON format is a JSON-B column.

17. The method of claim 15, wherein the request for an assessment form comprises an identity of the care giver role.

18. The method of claim 15, wherein the request for an assessment form comprises an identity of the assessment type.

19. The method of claim 15, further comprising changing the assessment template by adding at least one new human readable attribute-value pair to the assessment template, whereby a change is made to the assessment form created by the assessment component.

20. The method of claim 15, wherein the request for an assessment form is received from the patient care giver tool UI via a representational state transfer (REST) application programming interface (API) extended by the assessment component.

* * * * *